US012642775B2

(12) United States Patent
Atabekyan et al.

(10) Patent No.: US 12,642,775 B2
(45) Date of Patent: Jun. 2, 2026

(54) SUBSTRATE FOR DELIVERING A BIOLOGICALLY ACTIVE SUBSTANCE

(71) Applicant: PHILIP MORRIS PRODUCTS S.A., Neuchatel (CH)

(72) Inventors: Mari Liova Atabekyan, Yerevan (AM); Zoya Melik Farmazyan, Yerevan (AM); Stepan Grigor Grigoryan, Yerevan (AM); Laurent Lavanant, Evian-les-Bains (FR); Vigen Onik Topuzyan, Yerevan (AM)

(73) Assignee: Philip Morris Products S.A., Neuchatel (CH)

(*) Notice: Subject to any disclaimer, the term of this patent is extended or adjusted under 35 U.S.C. 154(b) by 393 days.

(21) Appl. No.: 18/285,550

(22) PCT Filed: Apr. 13, 2022

(86) PCT No.: PCT/EP2022/059917
§ 371 (c)(1),
(2) Date: Oct. 4, 2023

(87) PCT Pub. No.: WO2022/219063
PCT Pub. Date: Oct. 20, 2022

(65) Prior Publication Data

US 2024/0197648 A1 Jun. 20, 2024

(30) Foreign Application Priority Data

Apr. 15, 2021 (AM) .................................. 20210028

(51) Int. Cl.
*A61K 9/70* (2006.01)
*A24B 15/32* (2006.01)
(Continued)

(52) U.S. Cl.
CPC ............ *A61K 9/7084* (2013.01); *A24B 15/32* (2013.01); *A61K 9/007* (2013.01); *A61K 31/435* (2013.01);
(Continued)

(58) Field of Classification Search
CPC .................................................... A61K 9/7084
See application file for complete search history.

(56) References Cited

U.S. PATENT DOCUMENTS

| | | | |
|---|---|---|---|
| 5,785,978 | A | 7/1998 | Porter |
| 6,689,379 | B1 | 2/2004 | Bracht |

(Continued)

FOREIGN PATENT DOCUMENTS

| | | |
|---|---|---|
| EP | 0 449 748 | 10/1991 |
| RU | 2242971 | 12/2004 |

(Continued)

OTHER PUBLICATIONS

PCT International Search Report and Written Opinion for PCT/EP2022/059917 dated Aug. 31, 2022 (12 pages).

(Continued)

*Primary Examiner* — Benjamin J Packard
(74) *Attorney, Agent, or Firm* — Mueting Raasch Group

(57) ABSTRACT

A substrate (12) for delivering a biologically active substance, the substrate (12) comprising: a cross-linked silicone matrix formed by cross-linking a silicone polymer using at least one crosslinking agent comprising a tetraalkoxysilane, the cross-linked silicone matrix defining a plurality of domains, and a composition contained within the domains of the cross-linked silicone matrix, wherein the composition comprises: at least one monomeric glycol and at least one biologically active substance.

17 Claims, 1 Drawing Sheet

Figure 1:
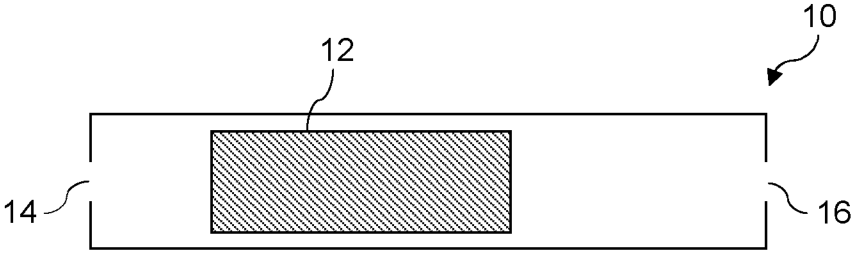

(51) Int. Cl.

| | | |
|---|---|---|
| *A61K 9/00* | (2006.01) | |
| *A61K 31/435* | (2006.01) | |
| *C08K 5/053* | (2006.01) | |
| *C08K 5/5415* | (2006.01) | |
| *C08L 83/04* | (2006.01) | |

(52) U.S. Cl.

CPC ............ *C08K 5/053* (2013.01); *C08K 5/5415* (2013.01); *C08L 83/04* (2013.01)

(56) References Cited

U.S. PATENT DOCUMENTS

| | | |
|---|---|---|
| 2014/0031734 A1 | 1/2014 | Saxena |
| 2018/0179340 A1 | 6/2018 | Skov |

FOREIGN PATENT DOCUMENTS

| | | |
|---|---|---|
| RU | 2382046 | 2/2010 |
| WO | WO 97/15295 | 5/1997 |

OTHER PUBLICATIONS

Michael A. Brook, Alison C. Holloway, Kenneth K. Ng, Michael Hrynyk, Carly Moore, Ryan Lall "Using a drug to structure its release matrix and release profile", International Journal of Pharmaceutics 358 (2008) 121-127).

Piotr Mazurek, Michael A. Brook, and Anne L. Skov. "Glycerol-Silicone Elastomers as Active Matrices with Controllable Release Profiles", Langmuire 2018, 34, 11559-11566.

P. Mazurek, S. Hvilsted, A.L. Skov. "Green silicone elastomer obtained from a counterintuitively stable mixture of glycerol and PDMS", Polymer, 87 (2016) 1-7.

Bruce J. Aungst "Nicotine skin penetration characteristics using aqueous & non-aqueous vehicles, anionic polymers, and silicone matrices", Drug development and industrial pharmacy, 14(11), 1481-1494 (1988).

J. E. Mark and J. L. Sullivan: "Model networks of end-linked polydimethylsiloxane chains. I. Comparisons between experimental and theoretical values of the elastic modulus and the equilibrium degree of swelling", J. Chern. Phys., vol. 66, No. 3, Feb. 1, 1977. www.chemspider.com/chemical-structure.57609370.html.

Office Action issued in Russia for Application No. 2023129406/04 dated Aug. 15, 2025 (27 pages). English translation included.

SUBSTRATE FOR DELIVERING A BIOLOGICALLY ACTIVE SUBSTANCE

This application is a U.S. National Stage Application of International Application No. PCT/EP2022/059917 filed Apr. 13, 2022, which was published in English on Oct. 20, 2022, as International Publication No. WO 2022/219063 A1. International Application No. PCT/EP2022/059917 claims priority to AM20210028 filed Apr. 15, 2021.

The invention relates to a substrate for delivering a biologically active substance, an aerosol-generating article comprising the substrate, a transdermal patch comprising the substrate, an oral delivery product comprising the substrate, and a method for manufacturing the substrate.

It is known to use silicone polymers to form substrates for delivering biologically active substances. For example, silicone polymers have been used in implantable systems and in topical applications to deliver a biologically active substance.

A silicone polymer may be used to form a silicone matrix comprising a biologically active substance releasably contained therein. Controlled release of the biologically active substance from the silicone matrix is desirable since the release of the biologically active substance from the silicone matrix may affect the delivery of the biologically active substance to a user.

It has previously been proposed to control the release of a biologically active substance from a silicone matrix through the incorporation of additives in the silicone matrix. For example, additives may be included in the silicone matrix to provide domains in which a biologically active substance may be releasably contained. However, the inclusion of additives may be undesirable. For example, certain additives may not have biocompatibility suitable for inclusion in substrates for delivering a biologically active substance to a user. The inclusion of certain additives may also undesirably increase manufacturing costs.

Forming a matrix from a silicone polymer may involve vulcanisation of the silicone polymer. This may require a long curing time. Vulcanisation of the silicone polymer may thereby hinder efficient manufacturing of a substrate comprising the silicone polymer.

It would be desirable to provide an improved substrate for delivering a biologically active substance. In particular, it would be desirable to provide a substrate for delivering a biologically active substance that may provide a controlled release profile of the biologically active substance and that may be manufactured efficiently.

The invention relates to a substrate for delivering a biologically active substance. The substrate may comprise a cross-linked silicone matrix. The cross-linked silicone matrix may be formed by cross-linking a silicone polymer using at least one crosslinking agent. The at least one crosslinking agent may comprise a tetraalkoxysilane. The cross-linked silicone matrix may define a plurality of domains. The substrate may comprise a composition. The composition may be contained within the domains of the cross-linked silicone matrix. The composition may comprise at least one monomeric glycol. The composition may comprise at least one biologically active substance.

According to the invention there is provided a substrate for delivering a biologically active substance, the substrate comprising: a cross-linked silicone matrix formed by cross-linking a silicone polymer using at least one crosslinking agent comprising a tetraalkoxysilane, the cross-linked silicone matrix defining a plurality of domains; and a composition contained within the domains of the cross-linked silicone matrix, wherein the composition comprises: at least one monomeric glycol and at least one biologically active substance.

The invention also relates to an aerosol-generating article comprising a substrate for delivering a biologically active substance. The substrate may comprise a cross-linked silicone matrix. The cross-linked silicone matrix may be formed by cross-linking a silicone polymer using at least one crosslinking agent. The at least one crosslinking agent may comprise a tetraalkoxysilane. The cross-linked silicone matrix may define a plurality of domains. The substrate may comprise a composition. The composition may be contained within the domains of the cross-linked silicone matrix. The composition may comprise at least one monomeric glycol. The composition may comprise at least one biologically active substance.

According to the invention there is provided an aerosol-generating article comprising a substrate for delivering a biologically active substance, the substrate comprising: a cross-linked silicone matrix formed by cross-linking a silicone polymer using at least one crosslinking agent comprising a tetraalkoxysilane, the cross-linked silicone matrix defining a plurality of domains; and a composition contained within the domains of the cross-linked silicone matrix, wherein the composition comprises: at least one monomeric glycol and at least one biologically active substance.

The invention also relates to a transdermal patch comprising a substrate for delivering a biologically active substance. The substrate may comprise a cross-linked silicone matrix. The cross-linked silicone matrix may be formed by cross-linking a silicone polymer using at least one crosslinking agent. The at least one crosslinking agent may comprise a tetraalkoxysilane. The cross-linked silicone matrix may define a plurality of domains. The substrate may comprise a composition. The composition may be contained within the domains of the cross-linked silicone matrix. The composition may comprise at least one monomeric glycol. The composition may comprise at least one biologically active substance.

According to the invention there is provided a transdermal patch comprising a substrate for delivering a biologically active substance, the substrate comprising: a cross-linked silicone matrix formed by cross-linking a silicone polymer using at least one crosslinking agent comprising a tetraalkoxysilane, the cross-linked silicone matrix defining a plurality of domains; and a composition contained within the domains of the cross-linked silicone matrix, wherein the composition comprises: at least one monomeric glycol and at least one biologically active substance.

The invention also relates to an oral delivery product comprising a substrate for delivering a biologically active substance. The substrate may comprise a cross-linked silicone matrix. The cross-linked silicone matrix may be formed by cross-linking a silicone polymer using at least one crosslinking agent. The at least one crosslinking agent may comprise a tetraalkoxysilane. The cross-linked silicone matrix may define a plurality of domains. The substrate may comprise a composition. The composition may be contained within the domains of the cross-linked silicone matrix. The composition may comprise at least one monomeric glycol. The composition may comprise at least one biologically active substance.

According to the invention there is provided an oral delivery product comprising a substrate for delivering a biologically active substance, the substrate comprising: a cross-linked silicone matrix formed by cross-linking a silicone polymer using at least one crosslinking agent comprising a tetraalkoxysilane, the cross-linked silicone matrix defining a plurality of domains; and a composition contained within the domains of the cross-linked silicone matrix, wherein the composition comprises: at least one monomeric glycol and at least one biologically active substance.

The invention also relates to a method of manufacturing a substrate for delivering a biologically active substance. The method may comprise mixing a silicone polymer, at least one monomeric glycol, at least one biologically active substance, and at least one crosslinking agent to form a mixture. The at least one crosslinking agent may comprise a tetraalkoxysilane. The method may comprise curing the mixture to form the substrate.

According to the invention there is provided a method of manufacturing a substrate for delivering a biologically active substance, the method comprising: mixing a silicone polymer, at least one monomeric glycol, at least one biologically active substance, and at least one crosslinking agent comprising a tetraalkoxysilane to form a mixture; and curing the mixture to form the substrate.

In the following description, any references to features or properties of the substrate for delivering a biologically active substance according to the invention also apply to the substrate of aerosol-generating articles according to the invention, the substrate of transdermal patches according to the invention, the substrate of oral delivery products according to the invention, and the method of manufacturing a substrate according to the invention, unless stated otherwise.

Providing a substrate comprising at least one monomeric glycol and a cross-linked silicone matrix formed by cross-linking a silicone polymer comprising a tetraalkoxysilane may advantageously facilitate controlled release of at least one biologically active substance from the substrate.

Providing a substrate comprising at least one monomeric glycol and a cross-linked silicone matrix formed by cross-linking a silicone polymer using at least one crosslinking agent comprising a tetraalkoxysilane may advantageously facilitate efficient manufacturing of the substrate. In particular, it has been surprisingly found that providing a substrate comprising at least one monomeric glycol and a cross-linked silicone matrix formed by cross-linking a silicone polymer using at least one crosslinking agent comprising a tetraalkoxysilane may advantageously reduce the curing time required for vulcanisation of the silicone polymer.

As used herein with reference to the invention, the term "aerosol-generating article" is used to describe an article comprising a substrate that is heated to generate an inhalable aerosol for delivery to a user.

A substrate comprising at least one monomeric glycol and a cross-linked silicone matrix formed by cross-linking a silicone polymer using at least one crosslinking agent comprising a tetraalkoxysilane may advantageously be thermostable at temperatures reached by the substrate during use of an aerosol-generating article comprising the substrate.

A substrate comprising at least one monomeric glycol and a cross-linked silicone matrix formed by cross-linking a silicone polymer using at least one crosslinking agent comprising a tetraalkoxysilane may exhibit desired mechanical properties for a transdermal patch comprising the substrate or an oral delivery product comprising the substrate. In particular, the elasticity of the substrate may be such that an oral delivery product comprising the substrate provides a user with a desired oral sensory experience during use.

A substrate comprising at least one monomeric glycol and a cross-linked silicone matrix formed by cross-linking a silicone polymer using at least one crosslinking agent comprising a tetraalkoxysilane may advantageously be molded into shapes and sizes suitable for oral delivery products comprising the substrate.

As used herein with reference to the invention, the term "cross-linked silicone matrix" is used to describe a three-dimensional network formed by cross-linking a silicone polymer.

As used herein with reference to the invention, the term "domains" is used to describe pores within a cross-linked silicone matrix. A composition may be contained within the domains of a cross-linked silicone matrix.

Unless otherwise stated, the percentages by weight of components of the substrate recited herein are based on the total weight of the substrate.

The percentage by weight of a component may be calculated by dividing the total weight of the component used to form the substrate by the total weight of the substrate, and multiplying by 100.

The substrate may be formed by cross-linking any suitable silicone polymer.

Preferably, the silicone polymer comprises a linear silicone polymer.

Preferably, the silicone polymer comprises a hydroxyl-terminated silicone polymer.

Preferably, the silicone polymer comprises a linear hydroxyl-terminated silicone polymer.

Suitable hydroxyl-terminated silicone polymers include, but are not limited to, hydroxyl-terminated polydialkylsiloxanes, such as hydroxyl-terminated polydimethylsiloxane (PDMS-OH) and hydroxyl-terminated polydiethylsiloxane, and hydroxyl-terminated polydiphenylsiloxane.

Preferably, the silicone polymer comprises hydroxyl-terminated polydimethylsiloxane.

The molecular weight of the silicone polymer may be selected based on desired mechanical properties of the substrate. For example, the molecular weight of the silicone polymer may be selected to achieve a desired flexibility of the substrate. This may be particularly advantageous for a transdermal patch comprising the substrate or an oral delivery product comprising the substrate.

The silicone polymer may have a molecular weight of at least about 25000 grams per mole, or at least about 30000 grams per mole, or at least about 35000 grams per mole.

The silicone polymer may have a molecular weight of up to about 60000 grams per mole, or up to about 55000 grams per mole, or up to about 50000 grams per mole.

The silicone polymer may have a molecular weight of between about 25000 grams per mole and about 60000 grams per mole, or between about 25000 grams per mole and about 55000 grams per mole, or between about 25000 grams per mole and about 50000 grams per mole.

The silicone polymer may have a molecular weight of between about 30000 grams per mole and about 60000 grams per mole, or between about 30000 grams per mole and about 55000 grams per mole, or between about 30000 grams per mole and about 50000 grams per mole.

The silicone polymer may have a molecular weight of between about 35000 grams per mole and about 60000 grams per mole, or between about 35000 grams per mole and about 55000 grams per mole, or between about 35000 grams per mole and about 50000 grams per mole.

The silicone polymer may be used in an amount of at least about 35 percent by weight, or at least about 40 percent by weight, or at least about 45 percent by weight to form the cross-linked silicone matrix.

The silicone polymer may be used in an amount of up to about 85 percent by weight, or up to about 80 percent by weight, or up to about 75 percent by weight to form the cross-linked silicone matrix.

The silicone polymer may be used in an amount of between about 35 percent and about 85 percent by weight, or between about 35 percent and about 80 percent by weight, or between about 35 percent and about 75 percent by weight to form the cross-linked silicone matrix.

The silicone polymer may be used in an amount of between about 40 percent and about 85 percent by weight, or between about 40 percent and about 80 percent by weight, or between about 40 percent and about 75 percent by weight to form the cross-linked silicone matrix.

The silicone polymer may be used in an amount of between about 45 percent and about 85 percent by weight, or between about 45 percent and about 80 percent by weight, or between about 45 percent and about 75 percent by weight.

The silicone polymer may be cross-linked using at least one crosslinking agent selected from the group consisting of tetraethyl orthosilicate (TEOS), silicon glycerate (Si-GLY), and silicon 1,2-propylene glycolate (Si-PGL).

As used herein with reference to the invention, "tetraethyl orthosilicate" and "TEOS" refer to the chemical compound having the chemical structure:

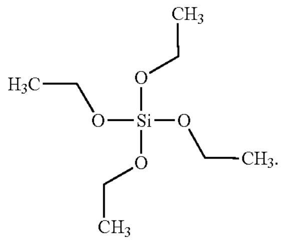

As used herein with reference to the invention, "silicon glycerate" and "Si-GLY" refer to the chemical compound having the chemical structure:

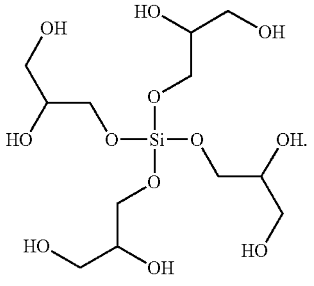 [SMILES: OCC(O)CO[Si](OCC(O)CO)(OCC(O)CO)OCC(O)CO]

As used herein with reference to the invention, "silicon 1,2-propylene glycolate" and "Si-PGL" refer to the chemical compound having the chemical structure:

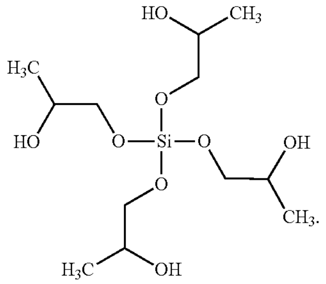 [SMILES: CC(O)CO[Si](OCC(C)O)(OCC(C)O)OCC(C)O]

Preferably, the at least one crosslinking agent comprises one or both of silicon glycerate and silicon 1,2-propylene glycolate. That is, preferably the at least one crosslinking agent comprises silicon glycerate, or silicon 1,2-propylene glycolate, or both silicon glycerate and silicon 1,2-propylene glycolate.

Cross-linking the silicone polymer using at least one crosslinking agent comprising one or both of silicon glycerate and silicon 1,2-propylene glycolate may advantageously substantially increase the rate of vulcanisation of the silicone polymer. This may advantageously facilitate efficient manufacturing of the substrate.

In certain embodiments, the at least one crosslinking agent preferably comprises silicon 1,2-propylene glycolate.

Where the at least one crosslinking agent comprises silicon glycerate, the silicon glycerate may be used in a solution with glycerol.

Where the silicon glycerate is used in a solution with glycerol, the solution may have a molar ratio of silicon glycerate to glycerol of between about 1:0.5 and about 1:2.9.

Where the at least one crosslinking agent comprises silicon 1,2-propylene glycolate, the silicon 1,2-propylene glycolate may be used in a solution with 1,2-propylene glycol.

Where the silicon 1,2-propylene glycolate is used in a solution with 1,2-propylene glycol, the solution may have a molar ratio of silicon 1,2-propylene glycolate to 1,2-propylene glycol of between about 1:0.5 and about 1:2.9.

Use of the at least one crosslinking agent in a solution with at least one monomeric glycol to form the substrate may influence the curing time required for vulcanisation of the silicone polymer.

The amount of crosslinking agent used to cross-link the silicone polymer may be selected based on a desired degree of vulcanisation of the silicone polymer. A high degree of vulcanisation of the silicone polymer may advantageously enhance the mechanical properties of the substrate.

An excess of crosslinking agent may be used to cross-link the silicone polymer.

The excess crosslinking agent may undergo hydrolysis to produce silicon dioxide during manufacturing of the substrate. Use of an excess of crosslinking agent to cross-link the silicone polymer may thereby advantageously reinforce the cross-linked silicone matrix. This may enhance the mechanical properties of the substrate.

Use of an excess of crosslinking agent to cross-link the silicone polymer may advantageously improve the reaction kinetics. This may increase the rate of vulcanisation of the silicone polymer.

The molar ratio of the at least one crosslinking agent to the silicone polymer may be at least about 1:2, or at least about 1:1, or at least about 2:1.

The molar ratio of the at least one crosslinking agent to the silicone polymer may be up to about 45:1, or up to about 40:1, or up to about 35:1.

The molar ratio of the at least one crosslinking agent to the silicone polymer may be between about 1:2 and about 45:1, or between about 1:2 and about 40:1, or between about 1:2 and about 35:1.

The molar ratio of the at least one crosslinking agent to the silicone polymer may be between about 1:1 and about 45:1, or between about 1:1 and about 40:1, or between about 1:1 and about 35:1.

The molar ratio of the at least one crosslinking agent to the silicone polymer may be between about 2:1 and about 45:1, or between about 2:1 and about 40:1, or between about 2:1 and about 35:1.

Where the at least one crosslinking agent comprises TEOS, the molar ratio of the TEOS to the silicone polymer may be at least about 5:1.

Where the at least one crosslinking agent comprises TEOS, the molar ratio of the TEOS to the silicone polymer may be up to about 35:1.

Where the at least one crosslinking agent comprises TEOS, the molar ratio of the TEOS to the silicone polymer may be between about 5:1 and about 35:1.

Where the at least one crosslinking agent comprises silicon glycerate, the molar ratio of the silicon glycerate to the silicone polymer may be at least about 5:1.

Where the at least one crosslinking agent comprises silicon glycerate, the molar ratio of the silicon glycerate to the silicone polymer may be up to about 20:1.

Where the at least one crosslinking agent comprises silicon glycerate, the molar ratio of the silicon glycerate to the silicone polymer may be between about 5:1 and about 20:1.

Where the at least one crosslinking agent comprises silicon 1,2-propylene glycolate, the molar ratio of the silicon 1,2-propylene glycolate to the silicone polymer may be at least about 2:1.

Where the at least one crosslinking agent comprises silicon 1,2-propylene glycolate, the molar ratio of the silicon 1,2-propylene glycolate to the silicone polymer may be up to about 5:1.

Where the at least one crosslinking agent comprises silicon 1,2-propylene glycolate, the molar ratio of the silicon 1,2-propylene glycolate to the silicone polymer may be between about 2:1 and about 5:1.

The at least one crosslinking agent may be used in an amount of at least about 0.5 percent by weight, or at least about 0.75 percent by weight, or at least about 1 percent by weight.

The at least one crosslinking agent may be used in an amount of up to about 18 percent by weight, or up to about 15 percent by weight, or up to about 12 percent by weight.

The at least one crosslinking agent may be used in an amount of between about 0.5 percent and about 18 percent by weight, or between about 0.5 percent and about 15 percent by weight, or between about 0.5 percent and about 12 percent by weight.

The at least one crosslinking agent may be used in an amount of between about 0.75 percent and about 18 percent by weight, or between about 0.75 percent and about 15 percent by weight, or between about 0.75 percent and about 12 percent by weight.

The at least one crosslinking agent may be used in an amount of between about 1 percent and about 18 percent by weight, or between about 1 percent and about 15 percent by weight, or between about 1 percent and about 12 percent by weight.

The substrate comprises a composition contained within the domains of the cross-linked silicone matrix. The composition comprises at least one monomeric glycol.

Inclusion of the at least one monomeric glycol may advantageously provide evenly dispersed domains within the cross-linked silicone matrix. This may advantageously result in the at least one biologically active substance being evenly dispersed within the cross-linked silicone matrix. This may advantageously help to achieve a controlled release profile of the at least one biologically active substance from the substrate.

Inclusion of the at least one monomeric glycol may provide hydrophilic domains within the cross-linked silicone matrix. The provision of hydrophilic domains within the cross-linked silicone matrix may advantageously facilitate manufacture of substrates according to the invention comprising hydrophilic biologically active substances.

Inclusion of the at least one monomeric glycol may advantageously avoid the need to include undesirable additives in the substrate. For example, inclusion of the at least one monomeric glycol may avoid the need to include polyethylene oxide (PEO) in the substrate. Inclusion of the at least one monomeric glycol may avoid the need to include fatty acids, such as linoleic acid and oleic acid, in the substrate.

Inclusion of at least one monomeric glycol may thereby advantageously enable cost effective and efficient manufacturing of a substrate for delivering a biologically active substance that provides a controlled release profile of the biologically active substance.

The at least one monomeric glycol may be selected based on desired properties of the domains of the cross-linked silicone matrix.

The at least one monomeric glycol may be selected based on a desired release profile of the at least one biologically active substance.

The monomeric glycol may include up to seven carbon atoms.

The monomeric glycol may include at least two carbon atoms. For example, the monomeric glycol may include between two carbon atoms and seven carbon atoms, or between two carbon atoms and six carbon atoms, or between two carbon atoms and five carbon atoms, or between two carbon atoms and four carbon atoms, or between two carbon atoms and three carbon atoms.

The monomeric glycol may include at least three carbon atoms. For example, the monomeric glycol may include between three carbon atoms and seven carbon atoms, or between three carbon atoms and six carbon atoms, or between three carbon atoms and five carbon atoms, or between three carbon atoms and four carbon atoms.

Preferably, the monomeric glycol includes three carbon atoms.

Suitable monomeric glycols include, but are not limited to, glycerol and 1,2-propylene glycol. The at least one monomeric glycol may comprise one or both of glycerol and 1,2-propylene glycol.

The at least one monomeric glycol may comprise glycerol.

The at least one monomeric glycol may comprise 1,2-propylene glycol.

The at least one monomeric glycol may comprise both glycerol and 1,2-propylene glycol.

In an aerosol-generating article comprising the substrate, glycerol and 1,2-propylene glycol may convey other compounds released from the substrate upon heating, such as the biologically active substance.

The at least one monomeric glycol in the composition may originate from a single source.

The at least one monomeric glycol in the composition may originate from multiple sources.

The at least one monomeric glycol may be added during manufacturing of the substrate separately from other components used to form the substrate.

The at least one monomeric glycol may be added during manufacturing of the substrate in combination with other components used to form the substrate. For example, the at least one monomeric glycol may be added during manufacturing of the substrate in combination with the at least one crosslinking agent. For example, the at least one crosslinking agent may be used in a solution with the at least one monomeric glycol.

The at least one monomeric glycol may form during manufacturing of the substrate. For example, where the at least one crosslinking agent comprises silicon glycerate, glycerol may form during vulcanisation of the silicone polymer. Where the at least one crosslinking agent comprises silicon 1,2-propylene glycolate, 1,2-propylene glycol may form during vulcanisation of the silicone polymer.

The substrate may comprise the at least one monomeric glycol in an amount of at least about 10 percent by weight, or at least about 15 percent by weight, or at least about 20 percent by weight.

The substrate may comprise the at least one monomeric glycol in an amount of up to about 60 percent by weight, or up to about 55 percent by weight, or up to about 50 percent by weight.

The substrate may comprise the at least one monomeric glycol in an amount of between about 10 percent and about 60 percent by weight, or between about 10 percent and about 55 percent by weight, or between about 10 percent and about 50 percent by weight.

The substrate may comprise the at least one monomeric glycol in an amount of between about 15 percent and about 60 percent by weight, or between about 15 percent and about 55 percent by weight, or between about 15 percent and about 50 percent by weight.

The substrate may comprise the at least one monomeric glycol in an amount of between about 20 percent and about 60 percent by weight, or between about 20 percent and about 55 percent by weight, or between about 20 percent and about 50 percent by weight.

The percentage by weight of the at least one monomeric glycol is calculated by dividing the total weight of the at least one monomeric glycol present in the substrate by the total weight of the substrate, and multiplying by 100. The total weight of the at least one monomeric glycol present in the substrate is calculated by adding together: the weight of any monomeric glycol added during manufacturing of the substrate separately from other components used to form the substrate; the weight of any monomeric glycol added during manufacturing of the substrate in combination with other components used to form the substrate, such as the at least one crosslinking agent; and the weight of any monomeric glycol that forms during manufacturing of the substrate.

Where the substrate comprises both glycerol and 1,2-propylene glycol, the substrate may comprise about the same amount of glycerol as 1,2-propylene glycol by weight. Where the substrate comprises both glycerol and 1,2-propylene glycol, preferably the substrate comprises more glycerol than 1,2-propylene glycol by weight.

Where the substrate comprises both glycerol and 1,2-propylene glycol, the substrate may comprise glycerol and 1,2-propylene glycol in a ratio of at least about 1:1 by weight, or at least about 1.5:1 by weight, or at least about 2:1 by weight.

Where the substrate comprises both glycerol and 1,2-propylene glycol, the substrate may comprise glycerol and 1,2-propylene glycol in a ratio of up to about 59:1 by weight, or up to about 40:1 by weight, or up to about 25:1 by weight.

Where the substrate comprises both glycerol and 1,2-propylene glycol, the substrate may comprise glycerol and 1,2-propylene glycol in a ratio of between about 1:1 and about 59:1 by weight, or between about 1:1 and about 40:1 by weight, or between about 1:1 and about 25:1 by weight.

Where the substrate comprises both glycerol and 1,2-propylene glycol, the substrate may comprise glycerol and 1,2-propylene glycol in a ratio of between about 1.5:1 and about 59:1 by weight, or between about 1.5:1 and about 40:1 by weight, or between about 1.5:1 and about 25:1 by weight.

Where the substrate comprises both glycerol and 1,2-propylene glycol, the substrate may comprise glycerol and 1,2-propylene glycol in a ratio of between about 2:1 and about 59:1 by weight, or between about 2:1 and about 40:1 by weight, or between about 2:1 and about 25:1 by weight.

Inclusion of more glycerol than 1,2-propylene glycol by weight may assist in formation of a homogeneous mixture during manufacturing of the substrate. This may advantageously result in more even dispersion of the composition within the cross-linked silicone matrix. This may also advantageously facilitate manufacturing of the substrate.

The substrate may comprise polyethylene oxide.

Preferably, the substrate comprises polyethylene oxide in an amount of less than about 1 percent by weight, or less than about 0.5 percent by weight, or less than about 0.1 percent by weight.

More preferably, the substrate does not comprise polyethylene oxide.

The substrate may comprise a fatty acid, such as linoleic acid and oleic acid.

Preferably, the substrate comprises a fatty acid in an amount of less than about 1 percent by weight, or less than about 0.5 percent by weight, or less than about 0.1 percent by weight.

More preferably, the substrate does not comprise a fatty acid.

Preferably, the substrate does not comprise linoleic acid.

Preferably, the substrate does not comprise oleic acid.

The cross-linked silicone matrix may be formed by cross-linking the silicone polymer in the presence of a curing catalyst.

The curing catalyst may be selected based on a desired curing rate of the silicone polymer.

The curing catalyst may comprise a room temperature vulcanisation catalyst.

The curing catalyst may comprise at least one of an aminopropyl-terminated silicone polymer, an amine, and a metal-based catalyst. Suitable aminopropyl-terminated silicone polymers include, but are not limited to, aminopropyl-terminated polydimethylsiloxane (PDMS-$NH_2$). Suitable amines include, but are not limited to, monoamines, such as monoethanolamine; and diamines, such as 1,6-hexamethylenediamine. Suitable metal-based catalysts include, but are not limited to, dibutyltin dilaurate and tin (II) octanoate.

Preferably, the curing catalyst comprises an aminopropyl-terminated silicone polymer, such as aminopropyl-terminated polydimethylsiloxane. Aminopropyl-terminated silicone polymers may be biocompatible and so may be suitable for inclusion in a substrate for delivering a biologically active substance. Use of a curing catalyst comprising an aminopropyl-terminated silicone polymer may thereby simplify manufacturing of the substrate and improve the efficiency of manufacturing of the substrate.

The aminopropyl-terminated silicone polymer may have a molecular weight of at least about 400 grams per mole, or at least about 600 grams per mole, or at least about 800 grams per mole.

The aminopropyl-terminated silicone polymer may have a molecular weight of up to about 3000 grams per mole, or up to about 2800 grams per mole, or up to about 2600 grams per mole.

The aminopropyl-terminated silicone polymer may have a molecular weight of between about 400 grams per mole and about 3000 grams per mole, or between about 400 grams per mole and about 2800 grams per mole, or between about 400 grams per mole and about 2600 grams per mole.

The aminopropyl-terminated silicone polymer may have a molecular weight of between about 600 grams per mole and about 3000 grams per mole, or between about 600 grams per mole and about 2800 grams per mole, or between about 600 grams per mole and about 2600 grams per mole.

The aminopropyl-terminated silicone polymer may have a molecular weight of between about 800 grams per mole and about 3000 grams per mole, or between about 800 grams per mole and about 2800 grams per mole, or between about 800 grams per mole and about 2600 grams per mole.

The substrate may comprise the curing catalyst.

The substrate may comprise the curing catalyst in an amount of at least about 0.2 percent by weight, or at least about 0.5 percent by weight, or at least about 0.8 percent by weight.

The substrate may comprise the curing catalyst in an amount of up to about 12 percent by weight, or up to about 10 percent by weight, or up to about 8 percent by weight.

The substrate may comprise the curing catalyst in an amount of between about 0.2 percent and about 12 percent by weight, or between about 0.2 percent and about 10 percent by weight, or between about 0.2 percent and about 8 percent by weight.

The substrate may comprise the curing catalyst in an amount of between about 0.5 percent and about 12 percent by weight, or between about 0.5 percent and about 10 percent by weight, or between about 0.5 percent and about 8 percent by weight.

The substrate may comprise the curing catalyst in an amount of between about 0.8 percent and about 12 percent by weight, or between about 0.8 percent and about 10 percent by weight, or between about 0.8 percent and about 8 percent by weight.

The curing catalyst may be present during formation of the cross-linked silicone matrix in an amount of at least about 0.2 percent by weight, or at least about 0.5 percent by weight, or at least about 0.8 percent by weight.

The curing catalyst may be present during formation of the cross-linked silicone matrix in an amount of up to about 12 percent by weight, or up to about 10 percent by weight, or up to about 8 percent by weight.

The curing catalyst may be present during formation of the cross-linked silicone matrix in an amount of between about 0.2 percent and about 12 percent by weight, or between about 0.2 percent and about 10 percent by weight, or between about 0.2 percent and about 8 percent by weight.

The curing catalyst may be present during formation of the cross-linked silicone matrix in an amount of between about 0.5 percent and about 12 percent by weight, or between about 0.5 percent and about 10 percent by weight, or between about 0.5 percent and about 8 percent by weight.

The curing catalyst may be present during formation of the cross-linked silicone matrix in an amount of between about 0.8 percent and about 12 percent by weight, or between about 0.8 percent and about 10 percent by weight, or between about 0.8 percent and about 8 percent by weight.

The substrate may comprise any suitable biologically active substance.

The biologically active substance may be a hydrophilic biologically active substance.

Suitable biologically active substances include, but are not limited to, alkaloids, cannabinoids, furazolidone, ganglefene hydrochloride, and sodium diclofenac.

Suitable cannabinoids include, but are not limited to, cannabidiol (CBD) and tetrahydrocannabinol (THC).

Preferably, the at least one biologically active substance comprises an alkaloid.

More preferably, the at least one biologically active substance comprises nicotine. Where the at least one biologically active substance comprises nicotine, the nicotine may be in the form of a nicotine salt. Preferably, the nicotine is in the form of a nicotine base.

In oral delivery products comprising the substrate, the at least one biologically active substance may comprise one or both of nicotine and a cannabinoid.

The substrate may comprise any suitable amount of the at least one biologically active substance.

The amount of the at least one biologically active substance may depend on a number of factors including, but not limited to, the nature of the at least one biologically active substance and the method of administration of the at least one biologically active substance.

The amount of the at least one biologically active substance present in the substrate may be selected based on a desired dosage of the biologically active substance.

The substrate may comprise the at least one biologically active substance in an amount of at least about 0.2 percent by weight, or at least about 0.5 percent by weight, or at least about 1 percent by weight.

The substrate may comprise the at least one biologically active substance in an amount of up to about 15 percent by weight, or up to about 12 percent by weight, or up to about 10 percent by weight.

The substrate may comprise the at least one biologically active substance in an amount of between about 0.2 percent and about 15 percent by weight, or between about 0.2 percent and about 12 percent by weight, or between about 0.2 percent and about 10 percent by weight.

The substrate may comprise the at least one biologically active substance in an amount of between about 0.5 percent and about 15 percent by weight, or between about 0.5 percent and about 12 percent by weight, or between about 0.5 percent and about 10 percent by weight.

The substrate may comprise the at least one biologically active substance in an amount of between about 1 percent and about 15 percent by weight, or between about 1 percent and about 12 percent by weight, or between about 1 percent and about 10 percent by weight.

Where the at least one biologically active substance comprises nicotine, the substrate may comprise the nicotine in an amount of up to about 5 percent by weight.

The biologically active substance may comprise a biologically active component and a non-biologically active component. For example, the biologically active substance may be in the form of a salt comprising a biologically active component and a non-biologically active counterion. As another example, the biologically active substance may be in the form of a complex comprising a biologically active component and a non-biologically active ligand.

The percentage by weight of the biologically active substance is calculated using the weight of the biologically active component of the biologically active substance, and not the weight of any non-biologically active components of the biologically active substance. For example, where the at least one biologically active substance comprises nicotine in the form of a nicotine salt, the percentage by weight of the at least one biologically active substance is calculated using the weight of nicotine. As another example, where the at least one biologically active substance comprises ganglefene hydrochloride, the percentage by weight of the at least one biologically active substance is calculated using the weight of ganglefene.

The substrate may comprise a flavourant.

Where the substrate comprises a flavourant, preferably the composition comprises the flavourant.

Suitable flavourants include, but are not limited to, menthol.

The composition is releasably contained within the domains of the cross-linked silicone matrix.

The cross-linked silicone matrix may be open-celled.

The composition may be released from the domains of the cross-linked silicone matrix by the action of heat.

The composition may be released from the domains of the cross-linked silicone matrix by the action of pressure.

The composition may be released from the domains of the cross-linked silicone matrix by the action of saliva.

The composition may be a liquid or a suspension.

The substrate may comprise the composition in an amount of at least about 10 percent by weight, or at least about 15 percent by weight, or at least about 20 percent by weight.

The substrate may comprise the composition in an amount of up to about 75 percent by weight, or up to about 72 percent by weight, or up to about 70 percent by weight.

The substrate may comprise the composition in an amount of between about 10 percent and about 75 percent by weight, or between about 10 percent and about 72 percent by weight, or between about 10 percent and about 70 percent by weight.

The substrate may comprise the composition in an amount of between about 15 percent and about 75 percent by weight, or between about 15 percent and about 72 percent by weight, or between about 15 percent and about 70 percent by weight.

The substrate may comprise the composition in an amount of between about 20 percent and about 75 percent by weight, or between about 20 percent and about 72 percent by weight, or between about 20 percent and about 70 percent by weight.

Aerosol-generating articles in which a substrate, such as a nicotine-containing substrate, is heated to generate an aerosol, rather than combusted, are known in the art. An aim of such "heated" aerosol-generating articles is to reduce known harmful smoke constituents of the type produced by the combustion and pyrolytic degradation of tobacco in conventional cigarettes.

Typically in heated aerosol-generating articles, an aerosol is generated by the transfer of heat from a heat source to a physically separate substrate. In use, volatile compounds are released and entrained in air drawn through the aerosol-generating article. As the released compounds cool, they condense to form an aerosol that may be inhaled by a user.

The invention relates to an aerosol-generating article comprising a substrate according to the invention.

The aerosol-generating article may comprise a heating element configured to heat the aerosol-generating substrate.

The aerosol-generating article may be configured to be used with an aerosol-generating device. The aerosol-generating device may comprise a heating element configured to heat the substrate of the aerosol-generating article.

The heating element of one or both of the aerosol-generating article and the aerosol-generating device may comprise one or more resistive heating elements, one or more inductive heating elements, or a combination thereof.

The invention relates to a transdermal patch comprising a substrate according to the invention.

The transdermal patch may comprise a backing layer. The substrate may be attached to the backing layer.

The transdermal patch may comprise an adhesive layer. The substrate may be positioned between the backing layer and the adhesive layer.

The invention relates to an oral delivery product comprising a substrate according to the invention. Examples of oral delivery products according to the invention include, but are not limited to, oral chews, oral lozenges, and oral pouch products.

The invention relates to a method of manufacturing a substrate according to the invention.

Preferably, the method comprises mixing the silicone polymer and the at least one monomeric glycol to form an emulsion. The method may further comprise combining the emulsion with the at least one biologically active substance and the at least one crosslinking agent comprising a tetraalkoxysilane to form the mixture.

Mixing the silicone polymer and the at least one monomeric glycol to form an emulsion prior to combining the emulsion with the at least one biologically active substance and the at least one crosslinking agent may advantageously result in a more homogenous mixture. This may advantageously contribute to the formation of a substrate with an even dispersion of the composition. This may advantageously facilitate manufacturing of the substrate.

The method may comprise mixing a curing catalyst with the silicone polymer, the at least one monomeric glycol, the at least one biologically active substance, and the at least one crosslinking agent to form the mixture.

Where the method comprises mixing the silicone polymer and the at least one monomeric glycol to form an emulsion prior to combining the emulsion with the at least one biologically active substance and the at least one crosslinking agent, the method may comprise mixing a curing catalyst with the emulsion, the at least one crosslinking agent, and the at least one biologically active substance to form the mixture.

The method may comprise curing the mixture at room temperature.

As used herein with reference to the invention, the term "room temperature" is used to describe a temperature of between about 20 degrees Celsius and about 30 degrees Celsius.

Below, there is provided a non-exhaustive list of non-limiting examples. Any one or more of the features of these examples may be combined with any one or more features of another example, or embodiment, or aspect described herein.

EX1: A substrate for delivering a biologically active substance, the substrate comprising:

a cross-linked silicone matrix formed by cross-linking a silicone polymer using at least one crosslinking agent comprising a tetraalkoxysilane, the cross-linked silicone matrix defining a plurality of domains; and a composition contained within the domains of the cross-linked silicone matrix, wherein the composition comprises:

at least one monomeric glycol; and at least one biologically active substance.

EX2: A substrate according to EX1 wherein the silicone polymer comprises a hydroxyl-terminated silicone polymer.

EX3: A substrate according to EX1 or EX2 wherein the silicone polymer comprises a hydroxyl-terminated polydialkylsiloxane.

EX4: A substrate according to any one of EX1 to EX3 wherein the silicone polymer comprises hydroxyl-terminated polydimethylsiloxane.

EX5: A substrate according to any one of EX1 to EX3 wherein the silicone polymer comprises hydroxyl-terminated polydiethylsiloxane.

EX6: A substrate according to EX1 or EX2 wherein the silicone polymer comprises hydroxyl-terminated polydiphenylsiloxane.

EX7: A substrate according to any one of EX1 to EX6 wherein the silicone polymer has a molecular weight of at least about 25000 grams per mole.

EX8: A substrate according to any one of EX1 to EX7 wherein the silicone polymer has a molecular weight of at least about 30000 grams per mole.

EX9: A substrate according to any one of EX1 to EX8 wherein the silicone polymer has a molecular weight of at least about 35000 grams per mole.

EX10: A substrate according to any one of EX1 to EX9 wherein the silicone polymer has a molecular weight of up to about 60000 grams per mole.

EX11: A substrate according to any one of EX1 to EX10 wherein the silicone polymer has a molecular weight of up to about 55000 grams per mole.

EX12: A substrate according to any one of EX1 to EX11 wherein the silicone polymer has a molecular weight of up to about 50000 grams per mole.

EX13: A substrate according to any one of EX1 to EX12 wherein the silicone polymer is used in an amount of at least about 35 percent by weight.

EX14: A substrate according to any one of EX1 to EX13 wherein the silicone polymer is used in an amount of at least about 40 percent by weight.

EX15: A substrate according to any one of EX1 to EX14 wherein the silicone polymer is used in an amount of at least about 45 percent by weight.

EX16: A substrate according to any one of EX1 to EX15 wherein the silicone polymer is used in an amount of up to about 85 percent by weight.

EX17: A substrate according to any one of EX1 to EX16 wherein the silicone polymer is used in an amount of up to about 80 percent by weight.

EX18: A substrate according to any one of EX1 to EX17 wherein the silicone polymer is used in an amount of up to about 75 percent by weight.

EX19: A substrate according to any one of EX1 to EX18 wherein the at least one crosslinking agent is selected from the group consisting of TEOS, silicon glycerate, and silicon 1,2-propylene glycolate.

EX20: A substrate according to any one of EX1 to EX19 wherein the at least one crosslinking agent comprises one or both of silicon glycerate and silicon 1,2-propylene glycolate.

EX21: A substrate according to any one of EX1 to EX20 wherein the at least one crosslinking agent comprises silicon glycerate.

EX22: A substrate according to EX21 wherein the silicon glycerate is used in a solution with glycerol.

EX23: A substrate according to EX22 wherein the solution has a molar ratio of silicon glycerate to glycerol of between about 1:0.5 and about 1:2.9.

EX24: A substrate according to any one of EX1 to EX23 wherein the at least one crosslinking agent comprises silicon 1,2-propylene glycolate.

EX25: A substrate according to EX24 wherein the silicon 1,2-propylene glycolate is used in a solution with 1,2-propylene glycol.

EX26: A substrate according to EX25 wherein the solution has a molar ratio of silicon 1,2-propylene glycolate to 1,2-propylene glycol of between about 1:0.5 and about 1:2.9.

EX27: A substrate according to any one of EX1 to EX26 wherein the molar ratio of the at least one crosslinking agent to the silicone polymer is at least about 1:2.

EX28: A substrate according to any one of EX1 to EX27 wherein an excess of the at least one crosslinking agent is used to cross-link the silicone polymer.

EX29: A substrate according to any one of EX1 to EX28 wherein the molar ratio of the at least one crosslinking agent to the silicone polymer is at least about 1:1.

EX30: A substrate according to any one of EX1 to EX29 wherein the molar ratio of the at least one crosslinking agent to the silicone polymer is at least about 2:1.

EX31: A substrate according to any one of EX1 to EX30 wherein the molar ratio of the at least one crosslinking agent to the silicone polymer is up to about 45:1.

EX32: A substrate according to any one of EX1 to EX31 wherein the molar ratio of the at least one crosslinking agent to the silicone polymer is up to about 40:1.

EX33: A substrate according to any one of EX1 to EX32 wherein the molar ratio of the at least one crosslinking agent to the silicone polymer is up to about 35:1.

EX34: A substrate according to any one of EX1 to EX33 wherein the at least one crosslinking agent comprises TEOS, and wherein the molar ratio of the TEOS to the silicon polymer is at least about 5:1.

EX35: A substrate according to any one of EX1 to EX34 wherein the at least one crosslinking agent comprises TEOS, and wherein the molar ratio of the TEOS to the silicon polymer is up to about 35:1.

EX36: A substrate according to any one of EX1 to EX35 wherein the at least one crosslinking agent comprises silicon glycerate, and wherein the molar ratio of the silicon glycerate to the silicone polymer is at least about 5:1.

EX37: A substrate according to any one of EX1 to EX36 wherein the at least one crosslinking agent comprises silicon glycerate, and wherein the molar ratio of the silicon glycerate to the silicone polymer is up to about 20:1.

EX38: A substrate according to any one of EX1 to EX37 wherein the at least one crosslinking agent comprises silicon 1,2-propylene glycolate, and wherein the molar ratio of the silicon 1,2-propylene glycolate to the silicone polymer is at least about 2:1.

EX39: A substrate according to any one of EX1 to EX38 wherein the at least one crosslinking agent comprises silicon 1,2-propylene glycolate, and wherein the molar ratio of the silicon 1,2-propylene glycolate to the silicone polymer is up to about 5:1.

EX40: A substrate according to any one of EX1 to EX39 wherein the substrate comprises silicon dioxide.

EX41: A substrate according to any one of EX1 to EX40 wherein the at least one crosslinking agent is used in an amount of at least about 0.5 percent by weight.

EX42: A substrate according to any one of EX1 to EX41 wherein the at least one crosslinking agent is used in an amount of at least about 0.75 percent by weight.

EX43: A substrate according to any one of EX1 to EX42 wherein the at least one crosslinking agent is used in an amount of at least about 1 percent by weight.

EX44: A substrate according to any one of EX1 to EX 43 wherein the at least one crosslinking agent is used in an amount of up to about 18 percent by weight.

EX45: A substrate according to any one of EX1 to EX44 wherein the at least one crosslinking agent is used in an amount of up to about 15 percent by weight.

EX46: A substrate according to any one of EX1 to EX45 wherein the at least one crosslinking agent is used in an amount of up to about 12 percent by weight.

EX47: A substrate according to any one of EX1 to EX46 wherein the monomeric glycol includes up to seven carbon atoms.

EX48: A substrate according to any one of EX1 to EX47 wherein the monomeric glycol includes at least two carbon atoms.

EX49: A substrate according to any one of EX1 to EX48 wherein the monomeric glycol includes between two carbon atoms and six carbon atoms.

EX50: A substrate according to any one of EX1 to EX49 wherein the monomeric glycol includes between two carbon atoms and five carbon atoms.

EX51: A substrate according to any one of EX1 to EX50 wherein the monomeric glycol includes between two carbon atoms and four carbon atoms.

EX52: A substrate according to any one of EX1 to EX51 wherein the monomeric glycol includes between two carbon atoms and three carbon atoms.

EX53: A substrate according to any one of EX1 to EX52 wherein the monomeric glycol includes at least three carbon atoms.

EX54: A substrate according to any one of EX1 to EX48 or EX53 wherein the monomeric glycol includes between three carbon atoms and seven carbon atoms.

EX55: A substrate according to any one of EX1 to EX49, EX53 or EX54 wherein the monomeric glycol includes between three carbon atoms and six carbon atoms.

EX56: A substrate according to any one of EX1 to EX50 or any one of EX53 to EX55 wherein the monomeric glycol includes between three carbon atoms and five carbon atoms.

EX57: A substrate according to any one of EX1 to EX51 or any one of EX53 to EX56 wherein the monomeric glycol includes between three carbon atoms and four carbon atoms.

EX58: A substrate according to any one of EX1 to EX57 wherein the monomeric glycol includes three carbon atoms.

EX59: A substrate according to any one of EX1 to EX58 wherein the at least one monomeric glycol comprises one or both of glycerol and 1,2-propylene glycol.

EX60: A substrate according to any one of EX1 to EX59 wherein the at least one monomeric glycol comprises glycerol.

EX61: A substrate according to any one of EX1 to EX60 wherein the at least one monomeric glycol comprises 1,2-propylene glycol.

EX62: A substrate according to any one of EX1 to EX61 wherein the substrate comprises the at least one monomeric glycol in an amount of at least about 10 percent by weight.

EX63: A substrate according to any one of EX1 to EX62 wherein the substrate comprises the at least one monomeric glycol in an amount of at least about 15 percent by weight.

EX64: A substrate according to any one of EX1 to EX63 wherein the substrate comprises the at least one monomeric glycol in an amount of at least about 20 percent by weight.

EX65: A substrate according to any one of EX1 to EX64 wherein the substrate comprises the at least one monomeric glycol in an amount of up to about 60 percent by weight.

EX66: A substrate according to any one of EX1 to EX65 wherein the substrate comprises the at least one monomeric glycol in an amount of up to about 55 percent by weight.

EX67: A substrate according to any one of EX1 to EX66 wherein the substrate comprises the at least one monomeric glycol in an amount of up to about 50 percent by weight.

EX68: A substrate according to any one of EX1 to EX67 wherein the substrate comprises glycerol and 1,2-propylene glycol in a ratio of greater than about 1:1 by weight.

EX69: A substrate according to any one of EX1 to EX68 wherein the substrate comprises both glycerol and 1,2-propylene glycol, and wherein the substrate comprises about the same amount of glycerol as 1,2-propylene glycol by weight.

EX70: A substrate according to any one of EX1 to EX68 wherein the substrate comprises both glycerol and 1,2-propylene glycol, and wherein the substrate comprises more glycerol than 1,2-propylene glycol by weight.

EX71: A substrate according to any one of EX1 to EX70 wherein the substrate comprises both glycerol and 1,2-propylene glycol, and wherein the substrate comprises glycerol and 1,2-propylene glycol in a ratio of at least about 1:1 by weight.

EX72: A substrate according to any one of EX1 to EX71 wherein the substrate comprises both glycerol and 1,2-propylene glycol, and wherein the substrate comprises glycerol and 1,2-proplyene glycol in a ratio of at least about 1.5:1 by weight.

EX73: A substrate according to any one of EX1 to EX72 wherein the substrate comprises both glycerol and 1,2-propylene glycol, and wherein the substrate comprises glycerol and 1,2-proplyene glycol in a ratio of at least about 2:1 by weight.

EX74: A substrate according to any one of EX1 to EX73 wherein the substrate comprises both glycerol and 1,2-propylene glycol, and wherein the substrate comprises glycerol and 1,2-proplyene glycol in a ratio of up to about 59:1 by weight.

EX75: A substrate according to any one of EX1 to EX74 wherein the substrate comprises both glycerol and 1,2-propylene glycol, and wherein the substrate comprises glycerol and 1,2-proplyene glycol in a ratio of up to about 40:1 by weight.

EX76: A substrate according to any one of EX1 to EX75 wherein the substrate comprises both glycerol and 1,2-propylene glycol, and wherein the substrate comprises glycerol and 1,2-proplyene glycol in a ratio of up to about 25:1 by weight.

EX77: A substrate according to any one of EX1 to EX76 wherein the substrate comprises polyethylene oxide.

EX78: A substrate according to any one of EX1 to EX77 wherein the substrate comprises polyethylene oxide in an amount of less than about 1 percent by weight.

EX79: A substrate according to any one of EX1 to EX78 wherein the substrate comprises polyethylene oxide in an amount of less than about 0.5 percent by weight.

EX80: A substrate according to any one of EX1 to EX79 wherein the substrate comprises polyethylene oxide in an amount of less than about 0.1 percent by weight.

EX81: A substrate according to any one of EX1 to EX76 wherein the substrate does not comprise polyethylene oxide.

EX82: A substrate according to any one of EX1 to EX81 wherein the substrate comprises a fatty acid.

EX83: A substrate according to any one of EX1 to EX82 wherein the substrate comprises a fatty acid in an amount of less than about 1 percent by weight.

EX84: A substrate according to any one of EX1 to EX83 wherein the substrate comprises a fatty acid in an amount of less than about 0.5 percent by weight.

EX85: A substrate according to any one of EX1 to EX84 wherein the substrate comprises a fatty acid in an amount of less than about 0.1 percent by weight.

EX86: A substrate according to any one of EX82 to EX85 wherein the fatty acid comprises linoleic acid.

EX87: A substrate according to any one of EX82 to EX86 wherein the fatty acid comprises oleic acid.

EX88: A substrate according to any one of EX1 to EX85 or EX87 wherein the substrate does not comprise linoleic acid.

EX89: A substrate according to any one of EX1 to EX86 or EX88 wherein the substrate does not comprise oleic acid.

EX90: A substrate according to any one of EX1 to EX81 wherein the substrate does not comprises a fatty acid.

EX91: A substrate according to any one of EX1 to EX90 wherein the substrate comprises a curing catalyst.

EX92: A substrate according to any one of EX1 to EX91 wherein the substrate comprises a curing catalyst in an amount of at least about 0.2 percent by weight.

EX93: A substrate according to any one of EX1 to EX92 wherein the substrate comprises a curing catalyst in an amount of at least about 0.5 percent by weight.

EX94: A substrate according to any one of EX1 to EX93 wherein the substrate comprises a curing catalyst in an amount of at least about 0.8 percent by weight.

EX95: A substrate according to any one of EX1 to EX94 wherein the substrate comprises a curing catalyst in an amount of up to about 12 percent by weight.

EX96: A substrate according to any one of EX1 to EX95 wherein the substrate comprises a curing catalyst in an amount up to about 10 percent by weight.

EX97: A substrate according to any one of EX1 to EX96 wherein the substrate comprises a curing catalyst in an amount of up to about 8 percent by weight.

EX98: A substrate according to any one of EX1 to EX97 wherein the cross-linked silicone matrix is formed by cross-linking the silicone polymer in the presence of a curing catalyst.

EX99: A substrate according to any one of EX1 to EX98 wherein a curing catalyst is present during formation of the cross-linked silicone matrix in an amount of at least about 0.2 percent by weight.

EX100: A substrate according to any one of EX1 to EX99 wherein a curing catalyst is present during formation of the cross-linked silicone matrix in an amount of at least about 0.5 percent by weight.

EX101: A substrate according to any one of EX1 to EX100 wherein a curing catalyst is present during formation of the cross-linked silicone matrix in an amount of at least about 0.8 percent by weight.

EX102: A substrate according to any one of EX1 to EX101 wherein a curing catalyst is present during formation of the cross-linked silicone matrix in an amount of up to about 12 percent by weight.

EX103: A substrate according to any one of EX1 to EX102 wherein a curing catalyst is present during formation of the cross-linked silicone matrix in an amount of up to about 10 percent by weight.

EX104: A substrate according to any one of EX1 to EX103 wherein a curing catalyst is present during formation of the cross-linked silicone matrix in an amount of up to about 8 percent by weight.

EX105: A substrate according to any one of EX91 to EX104 wherein the curing catalyst comprises a room temperature vulcanisation catalyst.

EX106: A substrate according to any one of EX91 to EX105 wherein the curing catalyst comprises at least one of an aminopropyl-terminated silicone polymer, an amine, and a metal-based catalyst.

EX107: A substrate according to any one of EX91 to EX106 wherein the curing catalyst comprises an aminopropyl-terminated silicone polymer.

EX108: A substrate according to any one of EX91 to EX107 wherein the curing catalyst comprises aminopropyl-terminated polydimethylsiloxane.

EX109: A substrate according to any one of EX91 to EX108 wherein the curing catalyst comprises an aminopropyl-terminated silicone polymer, and wherein the aminopropyl-terminated silicone polymer has a molecular weight of at least about 400 grams per mole.

EX110: A substrate according to any one of EX91 to EX109 wherein the curing catalyst comprises an aminopropyl-terminated silicone polymer, and wherein the aminopropyl-terminated silicone polymer has a molecular weight of at least about 600 grams per mole.

EX111: A substrate according to any one of EX91 to EX110 wherein the curing catalyst comprises an aminopropyl-terminated silicone polymer, and wherein the aminopropyl-terminated silicone polymer has a molecular weight of at least about 800 grams per mole.

EX112: A substrate according to any one of EX91 to EX111 wherein the curing catalyst comprises an aminopropyl-terminated silicone polymer, and wherein the aminopropyl-terminated silicone polymer has a molecular weight of up to about 3000 grams per mole.

EX113: A substrate according to any one of EX91 to EX112 wherein the curing catalyst comprises an aminopropyl-terminated silicone polymer, and wherein the aminopropyl-terminated silicone polymer has a molecular weight of up to about 2800 grams per mole.

EX114: A substrate according to any one of EX91 to EX113 wherein the curing catalyst comprises an aminopropyl-terminated silicone polymer, and wherein the aminopropyl-terminated silicone polymer has a molecular weight of up to about 2600 grams per mole.

EX115: A substrate according to any one of EX91 to EX114 wherein the curing catalyst comprises an amine.

EX116: A substrate according to any one of EX91 to EX115 wherein the curing catalyst comprises a monoamine.

EX117: A substrate according to any one of EX91 to EX116 wherein the curing catalyst comprises monoethanolamine.

EX118: A substrate according to any one of EX91 to EX116 wherein the curing catalyst comprises a diamine.

EX119: A substrate according to any one of EX91 to EX117 wherein the curing catalyst comprises 1,6-hexamethylenediamine.

EX120: A substrate according to any one of EX91 to EX119 wherein the curing catalyst comprises a metal-based catalyst.

EX121: A substrate according to any one of EX91 to EX120 wherein the curing catalyst comprises dibutyltin dilaurate.

EX122: A substrate according to any one of EX91 to EX121 wherein the curing catalyst comprises tin (II) octanoate.

EX123: A substrate according to any one of EX1 to EX122 wherein the at least one biologically active substance comprises an alkaloid.

EX124: A substrate according to any one of EX1 to EX123 wherein the at least one biologically active substance comprises nicotine.

EX125: A substrate according to EX124 wherein the nicotine is in the form of a nicotine salt.

EX126: A substrate according to EX124 wherein the nicotine is in the form of a nicotine base.

EX127: A substrate according to any one of EX1 to EX126 wherein the at least one biologically active substance comprises a cannabinoid.

EX128: A substrate according to any one of EX1 to EX127 wherein the at least one biologically active substance comprises sodium diclofenac.

EX129: A substrate according to any one of EX1 to EX128 wherein the at least one biologically active substance comprises ganglefene hydrochloride.

EX130: A substrate according to any one of EX1 to EX129 wherein the at least one biologically active substance comprises furazolidone.

EX131: A substrate according to any one of EX1 to EX130 wherein the substrate comprises the at least one biologically active substance in an amount of at least about 0.2 percent by weight.

EX132: A substrate according to any one of EX1 to EX131 wherein the substrate comprises the at least one biologically active substance in an amount of at least about 0.5 percent by weight.

EX133: A substrate according to any one of EX1 to EX132 wherein the substrate comprises the at least one biologically active substance in an amount of at least about 1 percent by weight.

EX134: A substrate according to any one of EX1 to EX133 wherein the substrate comprises the at least one biologically active substance in an amount of up to about 15 percent by weight.

EX135: A substrate according to any one of EX1 to EX134 wherein the substrate comprises the at least one biologically active substance in an amount of up to about 12 percent by weight.

EX136: A substrate according to any one of EX1 to EX135 wherein the substrate comprises the at least one biologically active substance in an amount of up to about 10 percent by weight.

EX137: A substrate according to any one of EX1 to EX136 wherein the at least one biologically active substance comprises nicotine, and wherein the substrate comprises the nicotine in an amount of up to about 5 percent by weight.

EX138: A substrate according to any one of EX1 to EX137 wherein the substrate comprises a flavourant.

EX139: A substrate according to any one of EX1 to EX138 wherein the composition comprises a flavourant.

EX140: A substrate according to EX138 or EX141 wherein the flavourant comprises menthol.

EX141: A substrate according to any one of EX1 to EX140 wherein the composition is releasably contained within the domains of the cross-linked silicone matrix.

EX142: A substrate according to any one of EX1 to EX141 wherein the composition is a liquid.

EX143: A substrate according to any one of EX1 to EX141 wherein the composition is a suspension.

EX144: A substrate according to any one of EX1 to EX143 wherein the substrate comprises the composition in an amount of at least about 10 percent by weight.

EX145: A substrate according to any one of EX1 to EX144 wherein the substrate comprises the composition in an amount of at least about 15 percent by weight.

EX146: A substrate according to any one of EX1 to EX145 wherein the substrate comprises the composition in an amount of at least about 20 percent by weight.

EX147: A substrate according to any one of EX1 to EX146 wherein the substrate comprises the composition in an amount of up to about 75 percent by weight.

EX148: A substrate according to any one of EX1 to EX147 wherein the substrate comprises the composition in an amount of up to about 72 percent by weight.

EX149: A substrate according to any one of EX1 to EX148 wherein the substrate comprises the composition in an amount of up to about 70 percent by weight.

EX 150: An aerosol-generating article comprising a substrate according to any one of EX1 to EX149.

EX151: An aerosol-generating article according to EX150 wherein the aerosol-generating article comprises a heating element configured to heat the aerosol-generating substrate.

EX152: An aerosol-generating article according to EX151 wherein the heating element comprises one or more resistive heating elements.

EX153: An aerosol-generating article according to EX151 or EX152 wherein the heating element comprises one or more inductive heating elements.

EX154: An aerosol-generating article according to any-one of EX150 to EX153 wherein the aerosol-generating article is configured to be used with an aerosol-generating device.

EX155: An aerosol-generating article according to EX154 wherein the aerosol-generating device comprise a heating element configured to heat the substrate of the aerosol-generating article.

EX156: An aerosol-generating article according to EX155 wherein the heating element of the aerosol-generating device comprises one or more resistive heating elements.

EX157: An aerosol-generating article according to EX155 or EX156 wherein the heating element of the aerosol-generating device comprises one or more inductive heating elements.

EX158: A transdermal patch comprising a substrate according to any one of EX1 to EX149.

EX159: A transdermal patch according to EX158 wherein the transdermal patch comprises a backing layer.

EX160: A transdermal patch according to EX159 wherein the substrate is attached to the backing layer.

EX161: A transdermal patch according to any one of EX158 to EX160 wherein the transdermal patch comprises an adhesive layer.

EX162: A transdermal patch according to any one of EX158 to EX161 wherein the transdermal patch comprises a backing layer and an adhesive layer, and wherein the substrate is positioned between the backing layer and the adhesive layer.

EX163: An oral delivery product comprising a substrate according to any one of EX1 to EX149.

EX164: An oral delivery product according to EX163 wherein the oral delivery product is an oral chew.

EX165: An oral delivery product according to EX163 wherein the oral delivery product is an oral lozenge.

EX166: An oral delivery product according to EX163 wherein the oral delivery product is an oral pouch product.

EX167: An oral delivery product according to any one of EX163 to EX166 wherein the at least one biologically active substance comprises nicotine.

EX168: An oral delivery product according to any one of EX163 to EX167 wherein the at least one biologically active substance comprises a cannabinoid.

EX169: A method of manufacturing a substrate for delivering a biologically active substance according to any one of EX1 to EX149, the method comprising: mixing a silicone polymer, at least one monomeric glycol, at least one biologically active substance, and at least one crosslinking agent comprising a tetraalkoxysilane to form a mixture, and curing the mixture to form the substrate.

EX170: A method according to EX169 wherein the method comprises mixing the silicone polymer and the at least one monomeric glycol to form an emulsion.

EX171: A method according to EX170 wherein the method further comprises combining the emulsion with the at least one biologically active substance and the at least one crosslinking agent comprising a tetraalkoxysilane to form the mixture.

EX172: A method according to any one of EX169 to EX171 wherein the method comprises mixing a curing catalyst with the silicone polymer, the at least one monomeric glycol, the at least one biologically active substance, and the at least one crosslinking agent to form the mixture.

EX173: A method according to EX170 or EX171 wherein the method comprising mixing a curing catalyst with the emulsion, the at least one crosslinking agent, and the at least one biologically active substance to form the mixture.

EX174: A method according to anyone of EX169 to EX173 wherein the method comprises curing the mixture at room temperature.

Seventeen substrates according to the invention (Examples 1 to 17) are prepared using a silicone polymer, at least one crosslinking agent, at least one monomeric glycol, at least one biologically active substance, and a curing catalyst.

To form the substrates, the silicone polymer and the at least one monomeric glycol are mixed in a glass beaker to form a smooth emulsion. The at least one crosslinking agent, the curing catalyst, and the at least one biologically active substance are added to the emulsion. The resulting mixture is left to cure at room temperature to form a substrate comprising a cross-linked silicone matrix and a composition contained within the domains of the cross-linked silicone matrix.

Table 1 shows the silicone polymer, the at least one crosslinking agent, the at least one monomeric glycol, the at least one biologically active substance, the curing catalyst, and the amounts of these components used to form the substrates of Examples 1 to 6.

In Examples 1 to 3, the hydroxyl-terminated polydimethylsiloxane (PDMS-OH) is provided by Aldrich and has a viscosity of between 2550 and 3570 centistokes.

In Example 4, the hydroxyl-terminated polydimethylsiloxane (PDMS-OH) is provided by Gelest and has a viscosity of 3500 centistokes.

In Examples 5 and 6, the hydroxyl-terminated polydimethylsiloxane (PDMS-OH) is provided by Gelest and has a viscosity of 2000 centistokes.

In Examples 3 and 6, the silicon glycerate (Si-GLY) is in a solution with glycerol in a molar ratio of about 1:2.9.

In Examples 4 and 5, the silicon 1,2-propylene glycolate (Si-PGL) is in a solution with 1,2-propylene glycol in a molar ratio of about 1:2.9.

In Examples 1 to 3, the aminopropyl-terminated polydimethylsiloxane (PDMS-$NH_2$) is provided by Aldrich and has a viscosity of 50 centistokes.

In Examples 4 to 6, the aminopropyl-terminated polydimethylsiloxane (PDMS-$NH_2$) is provided by Gelest and has a viscosity of between 10 and 15 centistokes.

Table 2 shows the curing time required for vulcanisation of the silicone polymer to form the substrates of Examples 1 to 6.

The substrate of Example 1 is a dense monolith with no trace of glycerol on the outer surface.

The substrate of Example 2 is a dense bulk substrate with no trace of glycerol on the outer surface.

The substrate of Example 3 is a dense bulk substrate with no trace of glycerol on the outer surface.

The substrate of Example 4 is a dense monolith with no trace of glycerol on the outer surface.

The substrate of Example 5 is a dense bulk substrate with no trace of glycerol on the outer surface.

The substrate of Example 6 is a dense bulk substrate, which does not adhere to paper.

Table 2 also shows the amount of nicotine released from the substrates of Examples 1 to 6 in a saline solution at room temperature after about five hours and after about 24 hours. The amount of nicotine released in the saline solution is measured by UV analysis of the saline solution after the substrate has been placed in the saline solution for the specified time period. The amount of nicotine released in the saline solution is used to calculate a percentage by weight reduction of nicotine in the saline solution based on the weight of nicotine added to form the substrate. After about 24 hours a negligible amount of nicotine is further released from the substrates of Examples 1 to 6 in a saline solution.

Table 2 also shows the release of nicotine from the substrates of Examples 1 and 2 in an air stream heated to a temperature of about 200° C. after about ten minutes. Heating the substrate of Example 1 to about 200° C. results in release of nicotine in an aerosol with glycerol. Heating the substrate of Example 2 to about 200° C. results in release of nicotine in an aerosol with both glycerol and 1,2-propylene glycol. The release of nicotine in the heated air stream is calculated by placing the substrate that has been subjected to an air stream heated to a temperature of about 200° C. for about ten minutes into a saline solution at room temperature, measuring the amount of nicotine released into the saline solution after about 24 hours by UV analysis, and subtracting the amount of nicotine released into the saline solution from the amount of nicotine used to form the substrate. The calculated amount of nicotine released in the heated air stream is used to calculate a percentage reduction by weight of nicotine in the heated air stream based on the weight of nicotine used to form the substrate.

Table 2 also shows the weight loss measured by thermogravimetric analysis coupled with mass spectrometry (TGA-MS) of the substrates of Examples 1 to 3 and 5 when heated to a temperature of about 300° C. The weight loss of the substrate of Examples 1 and 3 is attributed to the release of nicotine and glycerol. The weight loss of the substrate of Examples 2 and 5 is attributed to the release of nicotine, glycerol and 1,2-propylene glycol.

Table 2 also shows the Young's modulus of the substrates of Examples 1 and 2 measured using a tensile test.

In Example 8, the silicon 1,2-propylene glycolate (Si-PGL) is in a solution with 1,2-propylene glycol in a molar ratio of about 1:2.9.

In Example 9, the silicon glycerate (Si-GLY) is in a solution with glycerol in a molar ratio of about 1:2.9.

In Examples 7 to 10, the aminopropyl-terminated polydimethylsiloxane ($PDMS-NH_2$) is provided by Gelest and has a viscosity of between 10 and 15 centistokes.

Table 4 shows the curing time required for vulcanisation of the silicone polymer to form the substrates of Examples 7 to 10.

The substrate of Example 7 is a dense bulk substrate, which does not adhere to paper.

The substrate of Example 8 is a dense bulk substrate, which does not adhere to paper.

The substrate of Example 9 is a dense bulk substrate, which does not adhere to paper.

The substrate of Example 10 is a dense bulk substrate, which does not adhere to paper.

Table 4 shows the amount of sodium diclofenac released from the substrates of Examples 7 to 9 in ethanol at room

TABLE 1

| Example | Silicone polymer(s) | | Monomeric glycol(s) | | Crosslinking agent(s) | | Curing catalyst(s) | | Biologically active substance(s) | |
|---|---|---|---|---|---|---|---|---|---|---|
| 1 | PDMS-OH | 5.4 g | Glycerol | 4.5 g (48.9 mmol) | TEOS | 0.78 g (3.75 mmol) | $PDMS-NH_2$ (Mw ~2500 g/mol) | 0.84 g (0.33 mmol) | Nicotine | 0.135 g (0.83 mmol) |
| 2 | PDMS-OH | 5.4 g | Glycerol<br>1,2-propylene glycol | 3.15 g (34.2 mmol)<br>1.35 g (17.7 mmol) | TEOS | 0.78 g (3.75 mmol) | $PDMS-NH_2$ (Mw ~2500 g/mol) | 0.84 g (0.33 mmol) | Nicotine | 0.135 g (0.83 mmol) |
| 3 | PDMS-OH | 5.4 g | Glycerol | 4.5 g (48.9 mmol) | Si-GLY in glycerol | 0.75 g (1.13 mmol) | $PDMS-NH_2$ (Mw ~2500 g/mol) | 0.84 g (0.33 mmol) | Nicotine | 0.135 g (0.83 mmol) |
| 4 | PDMS-OH (Mw ~43500 g/mol) | 13.5 g (0.31 mmol) | Glycerol | 10.8 g (117 mmol) | Si-PGL in 1,2-propylene glycol | 0.525 g (0.96 mmol) | $PDMS-NH_2$ (Mw ~850-900 g/mol) | 0.24 g (0.26 mmol) | Nicotine | 0.27 g (1.5 mmol) |
| 5 | PDMS-OH (Mw ~36000 g/mol) | 5.4 g (0.15 mmol) | Glycerol | 4.5 g (48.9 mmol) | Si-PGL in 1,2-propylene glycol | 0.23 g (0.42 mmol) | $PDMS-NH_2$ (Mw ~850-900 g/mol) | 0.1 g (0.11 mmol) | Nicotine | 0.135 g (0.83 mmol) |
| 6 | PDMS-OH (Mw ~36000 g/mol) | 1.8 g (0.05 mmol) | Glycerol | 0.6 g (6.52 mmol) | Si-GLY in glycerol | 0.5 g (0.76 mmol) | $PDMS-NH_2$ (Mw ~850-900 g/mol) | 0.07 g (0.078 mmol) | Nicotine | 0.045 g (0.28 mmol) |

TABLE 2

| Example | Curing time | Nicotine release in a saline solution at room temperature: After 5 hrs | After 24 hrs | Nicotine release in an air stream at 200° C. after 10 mins | TGA-MS weight loss at 300° C. | Young's modulus |
|---|---|---|---|---|---|---|
| 1 | 2 days | 78% | 87% | 90% | 45.2% | 1540.6 Pa |
| 2 | 2 days | 72% | 83% | 92% | 43.2% | 1961.33 Pa |
| 3 | 1 hour | 73% | 80% | — | 46.2% | — |
| 4 | Few minutes | 68.4% | 86.8% | — | — | — |
| 5 | Few minutes | 72% | 87% | — | 46.8% | — |
| 6 | 3 hours | 53% | 63% | — | — | — |

Table 3 shows the silicone polymer, the at least one crosslinking agent, the at least one monomeric glycol, the at least one biologically active substance, the curing catalyst, and the amounts of these components used to form the substrates of Examples 7 to 10.

In Examples 7 to 10, the hydroxyl-terminated polydimethylsiloxane (PDMS-OH) is provided by Gelest and has a viscosity of 2000 centistokes.

temperature after about 5 hours and after about 24 hours. The amount of sodium diclofenac released in ethanol is measured by UV analysis of the ethanol after the substrate has been placed in the ethanol for the specified time period. The amount of sodium diclofenac released in ethanol is used to calculate a percentage by weight reduction of sodium diclofenac in ethanol based on the total weight of sodium diclofenac added to form the substrate.

Table 4 also shows the amount of sodium diclofenac released from the substrates of Examples 7 to 10 in a saline solution at room temperature after about five hours, after about 24 hours, and after about 8 days. The amount of sodium diclofenac released in the saline solution is measured by UV analysis of the saline solution after the substrate has been placed in the saline solution for the specified time period. The amount of sodium diclofenac released in the saline solution is used to calculate a percentage by weight reduction of sodium diclofenac in the saline solution based on the total weight of sodium diclofenac added to form the substrate.

TABLE 3

| Example | Silicone polymer(s) | | Monomeric glycol(s) | | Crosslinking agent(s) | | Curing catalyst(s) | | Biologically active substance(s) | |
|---|---|---|---|---|---|---|---|---|---|---|
| 7 | PDMS-OH (Mw ~36000 g/mol) | 1.8 g (0.05 mmol) | Glycerol | 0.6 g (6.52 mmol) | TEOS | 0.07 g (0.34 mmol) | PDMS-$NH_2$ (Mw ~850-900 g/mol) | 0.07 g (0.078 mmol) | Sodium diclofenac | 0.06 g (0.19 mmol) |
| 8 | PDMS-OH (Mw ~36000 g/mol) | 1.8 g (0.05 mmol) | Glycerol | 0.6 g (6.52 mmol) | Si-PGL in 1,2-propylene glycol | 0.1 g (0.18 mmol) | PDMS-$NH_2$ (Mw ~850-900 g/mol) | 0.07 g (0.078 mmol) | Sodium diclofenac | 0.06 g (0.19 mmol) |
| 9 | PDMS-OH (Mw ~36000 g/mol) | 1.8 g (0.05 mmol) | Glycerol | 0.6 g (6.52 mmol) | Si-GLY in glycerol | 0.5 g (0.76 mmol) | PDMS-$NH_2$ (Mw ~850-900 g/mol) | 0.07 g (0.078 mmol) | Sodium diclofenac | 0.06 g (0.19 mmol) |
| 10 | PDMS-OH (Mw ~36000 g/mol) | 1.8 g (0.05 mmol) | Glycerol | 0.6 g (6.52 mmol) | Si-GLY | 0.3 g (0.76 mmol) | PDMS-$NH_2$ (Mw ~850-900 g/mol) | 0.07 g (0.078 mmol) | Sodium diclofenac | 0.06 g (0.19 mmol) |

TABLE 4

| | | Sodium diclofenac release in ethanol at room temperature | | Sodium diclofenac release in saline at room temperature | | |
|---|---|---|---|---|---|---|
| Example | Curing time | After 5 hrs | After 24 hrs | After 5 hrs | After 24 hrs | After 8 days |
| 7 | 2 days | 20% | 68% | 6.4% | 14.1% | 35.5% |
| 8 | 1 hour | 68.5% | 98% | 9.8% | 19.4% | 43.8% |
| 9 | 30 mins | 61.5% | 98% | 11.1% | 29.1% | 70.2% |
| 10 | 1 day | — | — | 15.4% | 34.4% | 83.2% |

Table 5 shows the silicone polymer, the at least one crosslinking agent, the at least one monomeric glycol, the at least one biologically active substance, the curing catalyst, and the amounts of these components used to form the substrates of Examples 11 to 15.

In Examples 11 to 14, the hydroxyl-terminated polydimethylsiloxane (PDMS-OH) is provided by Gelest and has a viscosity of 2000 centistokes.

In Example 15, the hydroxyl-terminated polydimethylsiloxane (PDMS-OH) is provided by Gelest and has a viscosity of 5000 centistokes.

In Examples 12 and 15, the silicon 1,2-propylene glycolate (Si-PGL) is in a solution with 1,2-propylene glycol in a molar ratio of about 1:2.9.

In Example 13, the silicon glycerate (Si-GLY) is in a solution with glycerol in a molar ratio about 1:2.9.

In Examples 11 to 15, the aminopropyl-terminated polydimethylsiloxane (PDMS-$NH_2$) is provided by Gelest and has a viscosity of between 10 and 15 centistokes.

Table 6 shows the curing time required for vulcanisation of the silicone polymer to form the substrates of Examples 11 to 15.

The substrate of Example 11 is elastic and sticky and adheres strongly to paper.

The substrate of Example 12 is slightly sticky and adheres weakly to paper.

The substrate of Example 13 is slightly sticky, but does not adhere to paper.

The substrate of Example 14 is elastic and slightly sticky and adheres weakly to paper.

The substrate of Example 15 is elastic and slightly sticky and adheres weakly to paper.

Table 6 shows the amount of ganglefene hydrochloride released from the substrates of Examples 11 to 15 in a saline solution at room temperature after about 5 hours, after about 24 hours, and after about 8 days. The amount of ganglefene hydrochloride released in the saline solution is measured by UV analysis of the saline solution after the substrate has been placed in the saline solution for the specified time period. The amount of ganglefene hydrochloride released in the saline solution is used to calculate a percentage by weight reduction of ganglefene hydrochloride in the saline solution based on the weight of ganglefene hydrochloride added to form the substrate.

TABLE 5

| Example | Silicone polymer(s) | | Monomeric glycol(s) | | Crosslinking agent(s) | | Curing catalyst(s) | | Biologically active substance(s) | |
|---|---|---|---|---|---|---|---|---|---|---|
| 11 | PDMS-OH (Mw ~36000 g/mol) | 1.8 g (0.05 mmol) | Glycerol | 0.6 g (6.52 mmol) | TEOS | 0.07 g (0.34 mmol) | $PDMS-NH_2$ (Mw ~850-900 g/mol) | 0.07 g (0.078 mmol) | Ganglefene HCl | 0.06 g (0.16 mmol) |
| 12 | PDMS-OH (Mw ~36000 g/mol) | 1.8 g (0.05 mmol) | Glycerol | 0.6 g (6.52 mmol) | Si-PGL in 1,2-propylene glycol | 0.09 g (0.16 mmol) | $PDMS-NH_2$ (Mw ~850-900 g/mol) | 0.07 g (0.078 mmol) | Ganglefene HCl | 0.06 g (0.16 mmol) |
| 13 | PDMS-OH (Mw ~36000 g/mol | 1.8 g (0.05 mmol) | Glycerol | 0.6 g (6.52 mmol) | Si-GLY in glycerol | 0.5 g (0.76 mmol) | $PDMS-NH_2$ (Mw ~850-900 g/mol) | 0.14 g (0.15 mmol) | Ganglefene HCl | 0.06 g (0.16 mmol) |
| 14 | PDMS-OH (Mw ~36000 g/mol | 1.8 g (0.05 mmol) | Glycerol | 0.6 g (6.52 mmol) | Si-GLY | 0.3 g (0.76 mmol) | $PDMS-NH_2$ (Mw ~850-900 g/mol) | 0.07 g (0.078 mmol) | Ganglefene HCl | 0.06 g (0.16 mmol) |
| 15 | PDMS-OH (Mw ~49000 g/mol) | 2.45 g (0.05 mmol) | Glycerol | 0.6 g (6.52 mmol) | Si-PGL in 1,2-propylene glycol | 0.1 g (0.18 mmol) | $PDMS-NH_2$ (Mw ~850-900 g/mol) | 0.07 g (0.078 mmol) | Ganglefene HCl | 0.06 g (0.16 mmol) |

TABLE 6

| Example | Curing time | Ganglefene hydrochloride release in a saline solution at room temperature: After 5 hrs | After 24 hrs | After 8 days |
|---|---|---|---|---|
| 11 | 4 days | 10.7% | 17.3% | 46.8% |
| 12 | 4 hours | 8.8% | 14.6% | 43.3% |
| 13 | 6 hours | 3.3% | 4.6% | 17.0% |
| 14 | 1 day | 2.9% | 6.9% | 31.9% |
| 15 | 2 days | 17.8% | 28.8% | 44.8% |

Table 7 shows the silicone polymer, the at least one crosslinking agent, the at least one monomeric glycol, the at least one biologically active substance, the curing catalyst, and the amounts of these components used to form the substrates of Examples 16 and 17.

TABLE 7

| Example | Silicone polymer(s) | | Monomeric glycol(s) | | Crosslinking agent(s) | | Curing catalyst(s) | | Biologically active substance(s) | |
|---|---|---|---|---|---|---|---|---|---|---|
| 16 | PDMS-OH (Mw ~36000 g/mol) | 1.8 g (0.05 mmol) | Glycerol | 0.6 g (6.52 mmol) | Si-PGL in 1,2-propylene glycol | 0.09 g (0.16 mmol) | $PDMS-NH_2$ (Mw ~850-900 g/mol) | 0.07 g (0.078 mmol) | Furazolidone | 0.06 g (0.27 mmol) |
| 17 | PDMS-OH (Mw ~36000 g/mol) | 1.8 g (0.05 mmol) | Glycerol | 0.6 g (6.52 mmol) | Si-GLY in glycerol | 0.5 g (0.76 mmol) | $PDMS-NH_2$ (Mw ~850-900 g/mol) | 0.15 g (0.17 mmol) | Furazolidone | 0.06 g (0.27 mmol) |

In Examples 16 and 17, the hydroxyl-terminated polydimethylsiloxane (PDMS-OH) is provided by Gelest and has a viscosity of 2000 centistokes.

In Example 16, the silicon 1,2-propylene glycolate (Si-PGL) is in a solution with 1,2-propylene glycol in a molar ratio of about 1:2.9.

In Example 17, the silicon glycerate (Si-GLY) is in a solution with glycerol in a molar ratio of about 1:2.9.

In Examples 16 and 17, the aminopropyl-terminated polydimethylsiloxane ($PDMS-NH_2$) is provided by Gelest and has a viscosity of between 10 and 15 centistokes.

Table 8 shows the curing time required for vulcanisation of the silicone polymer to form the substrates of Examples 16 and 17.

The substrate of Example 16 is elastic and not sticky and adheres weakly to paper.

The substrate of Example 17 elastic and not sticky and adheres weakly to paper.

Table 8 also shows the amount of furazolidone released from the substrates of Examples 16 and 17 in a saline solution at room temperature after about 5 hours, after about 24 hours, and after about 8 days. The amount of furazolidone released in the saline solution is measured by UV analysis of the saline solution after the substrate has been placed in the saline solution for the specified time period. The amount of furazolidone released in the saline solution is used to calculate a percentage by weight reduction of furazolidone in the saline solution based on the weight of furazolidone added to form the substrate.

TABLE 8

| Example | Curing time | Furazolidone release in a saline solution at room temperature: After 5 hrs | After 24 hrs | After 8 days |
|---|---|---|---|---|
| 16 | 10 mins | 3.5% | 6.4% | 28.2% |
| 17 | 4 hours | 4.9% | 8.6% | 43.8% |

The invention will be further described, by way of example only, with reference to the accompanying drawings.

FIG. 1 shows a schematic side sectional view of an aerosol-generating article 10 comprising a substrate 12, an air inlet 14, and an air outlet 16.

Figure 2:
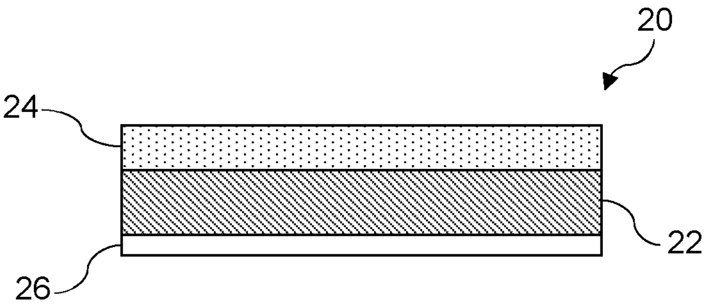

FIG. 2 shows a schematic side sectional view of a transdermal patch 20 comprising a substrate 22, a backing layer 24, and an adhesive layer 26. The substrate 22 is positioned between the backing layer 24 and the adhesive layer 26.

The specific embodiments and examples described above illustrate but do not limit the invention. It is to be understood that other embodiments of the invention may be made and the specific embodiments and examples described herein are not exhaustive.

The invention claimed is:

1. A substrate for delivering a biologically active substance, the substrate comprising:

a cross-linked silicone matrix formed by cross-linking a silicone polymer using at least one crosslinking agent comprising a tetraalkoxysilane, the cross-linked silicone matrix defining a plurality of domains; and a composition contained within the domains of the cross-linked silicone matrix, wherein the composition comprises:

at least one monomeric glycol; and at least one biologically active substance.

2. A substrate according to claim 1 wherein the at least one crosslinking agent is selected from the group consisting of TEOS, silicon glycerate, and silicon 1,2-propylene glycolate.

3. A substrate according to claim 2 wherein the at least one crosslinking agent comprises one or both of silicon glycerate and silicon 1,2-propylene glycolate.

4. A substrate according to claim 1 wherein the at least one crosslinking agent is used in an amount of between about 0.2 percent and about 18 percent by weight.

5. A substrate according to claim 1 wherein the at least one monomeric glycol comprises one or both of glycerol and 1,2-propylene glycol.

6. A substrate according to claim 1 wherein the substrate comprises the at least one monomeric glycol in an amount of between about 10 percent and about 60 percent by weight.

7. A substrate according to claim 1 wherein the silicone polymer comprises a hydroxyl-terminated silicone polymer.

8. A substrate according to claim 7 wherein the silicone polymer comprises hydroxyl-terminated polydimethylsiloxane.

9. A substrate according to claim 1 wherein the silicone polymer is used in an amount of between about 35 percent and about 85 percent by weight.

10. A substrate according to claim 1 wherein the substrate comprises a curing catalyst.

11. A substrate according to claim 10 wherein the curing catalyst comprises at least one of an aminopropyl-terminated silicone polymer, an amine, and a metal-based catalyst.

12. A substrate according to claim 10 wherein the substrate comprises the curing catalyst in an amount of between about 0.2 percent and about 12 percent by weight.

13. A substrate according to claim 1 wherein the substrate comprises the at least one biologically active substance in an amount of between about 0.2 percent and about 15 percent by weight.

14. A substrate according to claim 1 wherein the at least one biologically active substance comprises nicotine.

15. An aerosol-generating article comprising a substrate according to claim 1.

16. A transdermal patch comprising a substrate according to claim 1.

17. An oral delivery product comprising a substrate according to claim 1.

* * * * *